United States Patent
Kusibojoska et al.

(10) Patent No.: US 6,645,188 B2
(45) Date of Patent: Nov. 11, 2003

(54) ABSORBENT ARTICLE

(75) Inventors: Liljana Kusibojoska, Helsingborg (SE); Hans Een, Mölnlycke (SE)

(73) Assignee: SCA Hygiene Products AB, Goteborg (SE)

( * ) Notice: Subject to any disclaimer, the term of this patent is extended or adjusted under 35 U.S.C. 154(b) by 0 days.

(21) Appl. No.: 09/968,991

(22) Filed: Oct. 3, 2001

(65) Prior Publication Data

US 2002/0045882 A1 Apr. 18, 2002

Related U.S. Application Data

(60) Provisional application No. 60/240,955, filed on Oct. 18, 2000.

(30) Foreign Application Priority Data

Oct. 18, 2000 (SE) ................................................ 0003775

(51) Int. Cl.[7] ................................................ A61F 13/15
(52) U.S. Cl. ................................. 604/385.11; 604/392
(58) Field of Search ................................. 604/386, 387, 604/389, 390, 392, 401, 385.03, 385.11

(56) References Cited

U.S. PATENT DOCUMENTS

| | | | | |
|---|---|---|---|---|
| 4,346,700 A | * | 8/1982 | Dunshee et al. ............ 128/849 |
| 4,981,480 A | * | 1/1991 | Gaudet et al. ............... 604/386 |
| 5,074,854 A | * | 12/1991 | Davis ..................... 604/385.11 |
| 5,137,525 A | * | 8/1992 | Glassman .............. 604/385.11 |
| 5,397,319 A | * | 3/1995 | Suzuki et al. ........... 604/385.22 |
| 5,575,784 A | * | 11/1996 | Ames-Ooten et al. . 604/385.11 |
| 5,807,371 A | * | 9/1998 | Toyoda et al. .......... 604/385.29 |
| 5,944,707 A | * | 8/1999 | Ronn ......................... 604/386 |
| 6,102,899 A | * | 8/2000 | Yimin .................... 604/385.01 |
| 2002/0087132 A1 | * | 7/2002 | Samuelsson ................ 604/369 |
| 2002/0156447 A1 | * | 10/2002 | Boulanger et al. ...... 604/385.04 |
| 2002/0156448 A1 | * | 10/2002 | Steger et al. .......... 604/385.06 |

FOREIGN PATENT DOCUMENTS

| | | |
|---|---|---|
| EP | 0 287 388 A2 | 10/1988 |
| EP | 0 287 388 A3 | 10/1988 |
| EP | 0 528 282 A2 | 2/1993 |
| EP | 0 409 307 B1 | 9/1996 |
| EP | 0 605 012 B1 | 3/1999 |
| FR | 2 586 558 | 3/1987 |
| WO | 97/17926 | 5/1997 |
| WO | 98/47457 | 10/1998 |

* cited by examiner

Primary Examiner—Weilun Lo
Assistant Examiner—Michael G. Bogart
(74) Attorney, Agent, or Firm—Young & Thompson

(57) ABSTRACT

Absorbent article such as a diaper and an incontinence guard comprising a liquid permeable topsheet (2), a liquid impermeable backsheet (3) and an absorbent body (4) enclosed therebetween, the article having a front portion (5), a rear portion (6) and a crotch portion (7), therebetween, whereby the front and rear portion exhibits side flaps (8, 9), which are intended to attach the article to a pantlike shape around the waist of the user. The article comprises at least one attachment element (11) located on the rear portion (6) alternatively the front portion (5) of the article, close to an upper edge (6a, 6b) thereof, whereby the attachment element (11) is intended to be attached against the skin of the user to facilitate centering and application of the article on the user. Preferably the attachment element is arranged inside a perforated line, comprising an indication of fracture.

7 Claims, 2 Drawing Sheets

ABSORBENT ARTICLE

This application claims the benefit of U.S. Provisional Application No. 60/240,955, filed Oct. 18, 2000.

TECHNICAL FIELD

The present invention relates to an absorbent article such as a diaper and an incontinence guard comprising a liquid permeable topsheet, a liquid impermeable backsheet and an absorbent body enclosed therebetween, said article having a front portion, a rear portion and a crotch portion therebetween, whereby the front and rear portion exhibit side flaps, which are intended to attach the article together to a pantlike shape around the waist of the user.

BACKGROUND OF THE INVENTION

Diapers and incontinence guards for incontinent adults usually have a garment portion holding an absorbent body in place against the user's body and attachment means which hold the garment portion in place also when the user is moving. A common type of attachment means are adhesive tapes or hook and loop fasteners of the touch-and-close type which directly attach the front and rear portions of the absorbent article to each other. It is further known, through e.g., EP-A-0 287 388, EP-A-0 409 307, EP-A-0 528 282, EP-A-0 605 012 and FR-A-2 586 558, to attach the front and rear portions of the article by means of a belt, at which the possibilities to adjust the fit are improved. The belt further provides a simplified change of diaper or incontinence guard, especially when the patient is standing up.

One problem at application of so-called all-in-one diapers or belt diapers is to centre the diaper on the user. Especially when the patient is lying down and the nursing staff are forced to turn the patient several times to be able to apply the diaper, it may be difficult to get the centre of the diaper to lie close to the centre of the spine, since the diaper moves as the patient is being turned. Thus, the diaper often end up in a warped position, making it less effective as it should be, especially regarding sealing function and comfort.

Document WO 98/47457 discloses a diaper having inner adhesive surfaces intended to attach to the skin of the wearer. These function as a second fastening means at application of the product in combination with a first mechanical fastening means which finally attach the product on the patient. The main object is to achieve a good fit of the product against the skin for best sealing function but it does not describe how the product may be positioned on the wearer. Neither does it describe how to remove the adhesive surface after application of the diaper on the patient.

SUMMARY OF THE INVENTION

The object of the present invention is to accomplish an absorbent article, which may be positioned on the wearer to facilitate centering and application of the article on the user. This object is being solved in that the article comprises at least one attachment means being located on the rear portion alternatively the front portion of said article, close to an edge thereof, whereby said attachment means is intended to be attached against the skin of the wearer, at application of the article. Said attachment means allow a temporary adhering, ensuring the centering of the diaper on the patient at the subsequent application of the rest of the diaper. The diaper may also be provided with means for an easy removal of said attachment means after application of the entire product.

SHORT DESCRIPTION OF DRAWINGS

The invention will in the following be closer described with reference to an embodiment shown in the accompanying drawings.

DETAILED DESCRIPTION OF THE INVENTION

Figure 1:
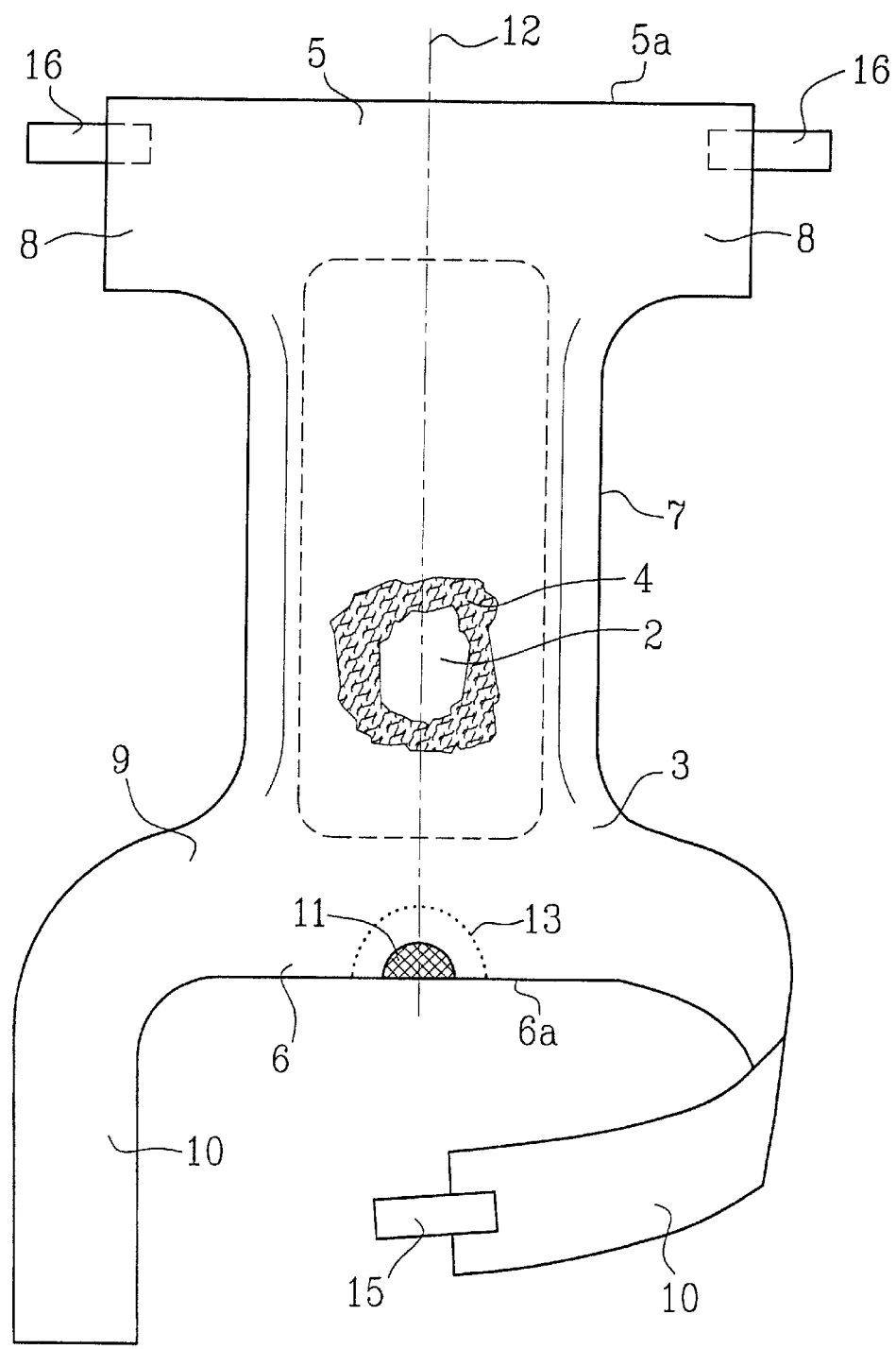
FIG. 1 shows schematically a perspective view of a diaper or incontinence guard according to the invention designed as a belt diaper.

The drawings show a couple of embodiments of diapers or incontinence guards 1, comprising a liquid impermeable backsheet 2, a liquid permeable topsheet 3 and an absorbent body 4 enclosed therebetween. The liquid permeable topsheet 3 may consist of a non-woven material, e.g. a spunbond material from continuous filaments, a meltblown material, a bonded carded fibrous web or a perforated plastic film. The liquid impermeable backsheet 2 may consist of a plastic film, a non-woven material coated with a liquid impervious material or a hydrophobic nonwoven material, which resists liquid penetration. The backsheet 2 and the topsheet 3 have a somewhat larger extension in the plane than the absorbent body 4 and extend beyond the edges of this. The layers 2 and 3 are mutually connected within the projecting portions, for example through joining using adhesive or welding using heat or ultra sonic.

The absorption body 4 may be of any conventional kind. Examples of common absorption materials are cellulosic fluff pulp, tissue layers, highly absorbent polymers (so-called superabsorbents), absorbent foam materials, absorbent non-woven materials or the like. It is common to combine cellulosic fluff pulp with superabsorbents in an absorbent body. It is also common to use absorbent bodies comprising layers of different materials having different properties with respect to liquid acquisition capacity, liquid distribution capacity and storage capacity. It is well known to the person skilled in the art and does therefore not have to be described in detail. The thin absorbent bodies, which are common in for instance baby diapers and incontinence guards, often consist of an compressed mixed or layered structure of cellulosic fluff pulp and superabsorbent.

The diaper/incontinence guard is intended to enclose the lower part of the wearer's trunk like a pair of absorbent pants. It comprises a front portion 5, intended during use to be worn on the front part of the user, a rear portion 6, intended during use to be worn on the rear part of the user, and a more narrow crotch portion 7 located between the front and rear portion, which is intended to be worn in the crotch part of the user between the legs. The diaper according to the invention is provided with a piece of adherent tape placed on the rear portion 6 of the diaper. The diaper may be a so called belt diaper, as shown in FIG. 1 or a so called all-in-one diaper as shown on FIG. 2.

FIG. 1 show a diaper according to the invention designed as a belt diaper. The front portion alternatively the rear portion 6 exhibit side flaps 8, which can be provided with a kind of fastenings means 16, such as adhesive tape portions or hooks and loops fasteners. The rear portion 6 alternatively the front portion 5 is also provided with side flaps 9, which in the embodiment shown in FIG. 1 are extended with a pair of belt portions 10, whereof at least one at its end portion is provided with a fastening means 15, such as adhesive tape portions or hooks and loops fastener. The belt parts 10 are intended to be attached in front of the waist of the wearer by means of fastening means 15. The front portion 5 alternatively the rear portion 6 are then attached to the belt parts 10 by means of fastening means 16 at the side flaps 8 of the front portion 5 alternatively the rear portion 6.

A pair of belt portions 10 are with one end attached, e.g., glued or ultrasonically welded, to the rear portion 6 alternatively the front portion 5 of the diaper. The belt portions 10 are with their opposite ends intended to be fastened together, by means of fastening means 15, such as hook and loop type fasteners or tape tabs, which is attached against the outside of the opposite belt portion. The fastening means 16 of the front portion 5 such as hook and loop type fasteners or tape tabs, is intended to be attached against the outsides of the belt portions 10 in order to fasten together the diaper/incontinence guard to the desired pantlike shape.

The width of the belt portions 10 should be between 5–20 cm, preferably between 7–15 cm. The belt portions 10 are preferably a laminate of a carrier material, which forms the outside of the belt, and a soft nonwoven, which forms the inside of the belt intended to be in direct contact with the skin of the user. A suitable nonwoven material can be a spunbond material of e.g., polypropylene- or polyethylene fibres. Conjugate fibres may also be used. Another suitable nonwoven material can be a carded thermobonded material of e.g., polypropylene-, polyester- or conjugate fibres. As carrier material there can be used a plastic film or another appropriate material, e.g., a nonwoven. The carrier material should be adapted to function as a reception surface for both the fastening means 15 and 16, wherein in those cases the attachment means are tape tabs, a plastic film is suitable. In those cases other types of fastening means are used instead of tape tabs, e.g., hook-and-loop type fasteners, another type of carrier material which may function as a reception surface for the fastening means, is preferably used. Also elastic laminates are suitable to use as material in the belt portions.

Figure 2:
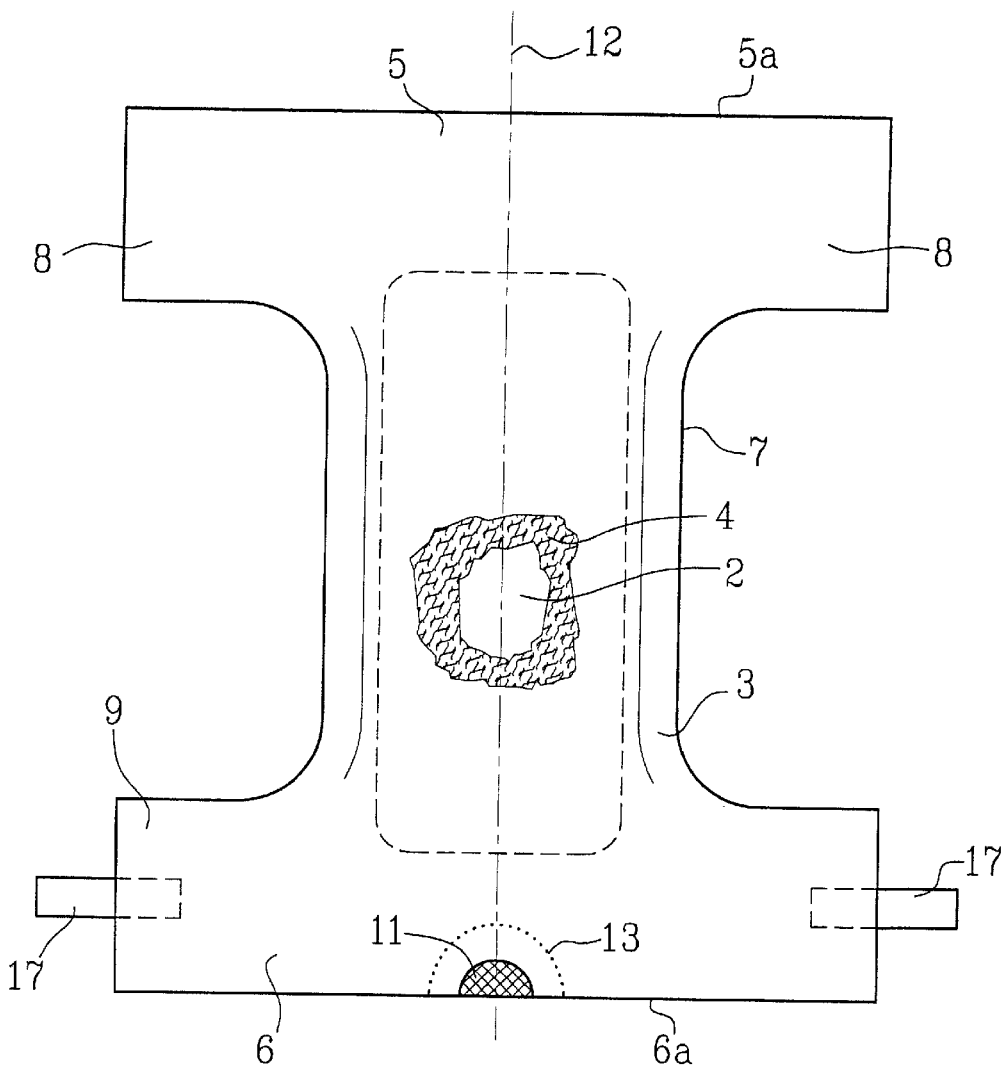
FIG. 2 shows schematically a perspective view of a diaper or incontinence guard according to the invention designed as an all-in-one diaper.
Figure 3:
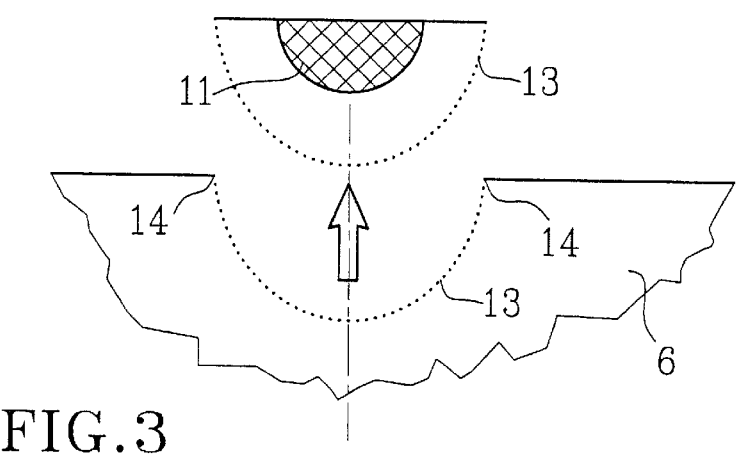
FIG. 3 shows the rear portion of a diaper according to the invention.

FIG. 2 show the diaper according to the invention designed as an all-in-one diaper, where the fastening means 17 preferably is located on the side flaps 9 on the rear portion 6. At application said fastening means 17 is attached to the front portion to form, the pantlike structure. The fastening means 17 may comprise hook and loop fasteners or tape tabs. The material on the front portion has the capability to function as reception surface for said fastening means 17.

The diaper according to the invention is provided with attachment means 11. The diaper may be a belt diaper, as shown in FIG. 1 or an all-in-one diaper, as shown in FIG. 2. Said attachment means 11 are preferably located on a portion on the rear portion 6 of the diaper. Said portion is preferably situated essentially on an imagined center line 12 on the diaper. Preferably this portion is located close to the upper edge 6a of the rear portion 6. The attachment means 11 may consist of a piece of adherent tape, a bead of adhesive, adhesive dot or the like. Said attachment means 11 is intended to temporarily attach the product at application via the rear portion 6 directly on the patient's skin at the back.

For a belt diaper, the attachment means 11 on the rear portion 6 is firstly attached directly to the skin on the back of the patient. Then the belt portions 10 are attached around the waist and further as described above. For a all-in-one diaper, the attachment means 11 on the rear portion 6 is applied directly to the skin on the back of the patient. Then the rest of the diaper is applied as described above. Thus, a good centering of the product on the patient is obtained. Since it is not recommended with a long term exposure of adhesive or the like directly to the skin, is it therefore desirable to be able to remove this attachment means 11 easily after it has fulfilled its duty. Thus, the attachment means 11 may be removed by for instance tear it off along a suitably arranged perforated line 13. This perforated line 13 is arranged inside and on a appropriate distance from said attachment means 11. Preferably said line 13 extend essentially in a U-shape, such as its ends 14 run out to the upper edge 6a of the rear portion 6 of the diaper. In the case where the attachment means 11 are arranged on the front portion 5, the ends 14 extend to the upper edge 5a of the front portion 5. Of course, said line 13 may also essentially extend in a V-shape. The main thing is that the design of the line 13 allows a simple removal of the attachment means 11.

Another advantage is obtained in that case where a belt diaper is concerned and this is applied on a standing patient having a large waist size. It can then be difficult for the nursing staff to reach around the patient in order to apply the belt portions 10 around the waist. The device according to the invention may facilitate application of the diaper in that one first apply said attachment means 11 on the patient and then is able to grasp the belt portions 10 using both hands to be able to apply the diaper in a correct way.

The invention is of course not limited to the above described embodiment but can be modified within the scope of the claims.

What is claimed is:

1. Absorbent article comprising:
   a liquid permeable topsheet, a liquid impermeable backsheet and an absorbent body enclosed therebetween;
   a front portion, a rear portion and a crotch portion therebetween;
   the front and rear portions having side flaps, which are intended to attach the article together to a pant shape around the waist of a user;
   at least one attachment means located in a region of one of the rear portion and the front portion of said article, close to an upper edge thereof;
   said attachment means being structured and arranged to be attached to the skin of the user during application of the article; and
   said attachment means being arranged inside a perforated line, comprising an indication of fracture, along which line, the region of the article exhibiting the attachment means may be removed from the rest of the article.

2. The absorbent article according to claim 9, wherein said region of said attachment means essentially lies on an imagined longitudinally center line of the article.

3. The absorbent article according to claim 9, wherein said attachment means comprise a piece of adherent tape or adhesive portion.

4. The absorbent article according to claim 9, wherein said perforated line is essentially U-shaped.

5. The absorbent article according to claim 9, wherein said perforated line is essentially V-shaped.

6. The absorbent article according to claim 9, wherein the article is a belt diaper, in which a pair of belt portions are connected to the side flaps of the rear or front portion;
   said belt portions intended to be attached around the waist of the user, and the side flaps of the opposite portion intended to be attached to the belt portions via attachment means.

7. The absorbent article according to claim 9, wherein the article is an all-in-one diaper, and the side flaps of the rear or front portion exhibit attachment means intended to be attached to the opposite portion.

* * * * *